(12) United States Patent
Miles et al.

(10) Patent No.: US 9,863,975 B2
(45) Date of Patent: Jan. 9, 2018

(54) FEMTOSECOND LASER EXCITATION TAGGING ANEMOMETRY

(75) Inventors: Richard B Miles, Princeton, NJ (US);
Arthur Dogariu, Hamilton, NJ (US);
James B Michael, Ames, IA (US);
Matthew R Edwards, Santa Monica, CA (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 404 days.

(21) Appl. No.: 14/115,129

(22) PCT Filed: May 3, 2012

(86) PCT No.: PCT/US2012/036343
§ 371 (c)(1),
(2), (4) Date: Nov. 1, 2013

(87) PCT Pub. No.: WO2012/151411
PCT Pub. Date: Nov. 8, 2012

(65) Prior Publication Data
US 2014/0071256 A1     Mar. 13, 2014

Related U.S. Application Data

(60) Provisional application No. 61/482,015, filed on May 3, 2011.

(51) Int. Cl.
*G01P 5/18* (2006.01)
*G01F 1/708* (2006.01)
(Continued)

(52) U.S. Cl.
CPC .............. *G01P 5/18* (2013.01); *G01F 1/7086* (2013.01); *G01P 5/001* (2013.01); *G01S 17/107* (2013.01);
(Continued)

(58) Field of Classification Search
CPC .......... G01F 1/7086; G01P 5/18; G01P 5/001; G01S 17/107; G01S 17/95; G01S 17/58; G01S 17/74; G01N 21/6456
See application file for complete search history.

(56) References Cited

U.S. PATENT DOCUMENTS 5,110,204 A * 5/1992 Miles ..................... G01P 5/20
356/28
5,333,044 A * 7/1994 Shaffer ................ A61B 5/0261
250/356.1
(Continued)

OTHER PUBLICATIONS

L.R. Boedeker, "Velocity measurement by H2O photolysis and laser-induced fluorescence of OH," Opt. Lett. vol. 14, No. 10; 473-475 (May 15, 1989).
(Continued)

*Primary Examiner* — Hesham Abouzahra
(74) *Attorney, Agent, or Firm* — Meagher Emanuel Laks Goldberg & Liao, LLP

(57) ABSTRACT

An apparatus for the imaging of gaseous fluid motion is disclosed. The apparatus includes a sub-nanosecond pulsed laser. The sub-nanosecond pulsed laser is configured to cause a particle species to fragment and for the recombining fragments subsequently to fluoresce. The apparatus also includes a gaseous fluid comprised of particle species. The apparatus also includes a time gated camera. The time gated camera configured to capture at least one image of the fluorescence from the recombining particle fragment species displaced after a specific time lapse following the laser pulse. Additionally, a fluid velocity can be calculated from a comparison of the image of the displaced particle species to an initial reference position and the time lapse. A Femtosecond Laser Electronic Excitation Tagging (FLEET) method of using the disclosed apparatus is also disclosed.

36 Claims, 12 Drawing Sheets

(51) Int. Cl.
 G01P 5/00 (2006.01)
 G01S 17/58 (2006.01)
 G01S 17/10 (2006.01)
 G01S 17/74 (2006.01)
 G01S 17/95 (2006.01)
 G01N 21/64 (2006.01)

(52) U.S. Cl.
 CPC .............. *G01S 17/58* (2013.01); *G01S 17/74* (2013.01); *G01S 17/95* (2013.01); *G01N 21/6456* (2013.01)

(56) References Cited

U.S. PATENT DOCUMENTS

| | | | | |
|---|---|---|---|---|
| 5,708,495 | A | * | 1/1998 | Pitz ........................... G01P 5/18 250/356.1 |
| 2010/0078576 | A1 | * | 4/2010 | Ntziachristos ....... A61B 5/0073 250/459.1 |
| 2010/0286674 | A1 | * | 11/2010 | Ben-Yakar ........... A61B 5/0059 606/10 |

OTHER PUBLICATIONS

N. Dam, R.J.H. Klein-Douwel, N.M. Sijtsema, and J.J. Ter Meulen, "Nitric oxide flow tagging in unseeded air," Opt. Lett. vol. 26, No. 1; 36-38 (Jan. 1, 2001).

B. Hiller, R.A. Booman, C. Hassa, and R.K. Hanson, "Velocity visualization in gas flows using laser-induced phosphorescence of biacetyl," Rev. Sci. Inst. 55; 1964-1967 (1984).

W.R. Lempert, P. Ronney, K. Magee, R. Gee, and R.P. Haughland, "Flow tagging velocimetry in incompressible flow using photo-activated nonintrusive tracking of molecular motion (PHANTOMM)," Exp. in Fluids 18; 249-257 (1995).

F. Martin, R. Mawassi, F. Vidal, I. Gallimberti, D. Comtois, H. Pepin, J.C. Kieffer, and H.P. Mercure, "Spectroscopic study of ultrashort pulse laser-breakdown plasmas in air," Appl. Spec. vol. 56, No. 11; 1444-1452 (2002).

R.B. Miles, J.J. Connors, E.C. Markovitz, P.J. Howard and G.J. Roth, "Instantaneous profiles and turbulence statistics of supersonic free shear layers by Raman excitation plus laser-induced electronic fluorescence (RELIEF)," Exp. in Fluids 8; 17-24 (1989).

R. Miles, C. Cohen, P. Howard, S. Huang, E. Markovitz, and G. Russell, "Velocity Measurements by vibrational tagging and fluorescent probing of oxygen," Opt. Lett. vol. 12, No. 11; 861-863 (Nov. 1987).

R.B. Miles, J. Connors, E. Markovitz, P. Howard and G. Roth, "Instantaneous supersonic velocity profiles in an underexpanded jet by oxygen flow tagging," Phys. Fluids A 1; 389-393 (Feb. 1989).

R.B. Miles, J. Grinstead, R.H. Kohl, and G. Diskin, "The RELIEF flow tagging technique and its application in engine testing facilities and in helium-air mixing studies," Meas. Sci. Tech. 11; 1272-1281 (2000).

A. Noullez, G. Wallace, W. Lempert, R.B. Miles and U. Frisch, "Transverse velocity increments in tubulent flow using the RELIEF technique," J. Fluid Mech. vol. 339; 287-307 (1997).

R.W. Pitz, J.A. Wehrmeyer, L.A. Ribarov, D.A. Oguss, F.B. Batliwala, P.A. Debarber, S. Deusch and P.E. Dimotakis, "Unseeded molecular flow tagging in cold and hot flows using ozone and hydroxyl tagging velocimetry," Meas. Sci. and Tech. 11; 1259-1271 (2000).

R.W. Pitz, T.M. Brown, S.P. Nandula, P.A. Skaggs, P.A. Debarber, M.S. Brown, and J. Segall, "Unseeded velocity measurement by ozone tagging velocimetry," Opt. Lett. vol. 21, No. 755-757 (May 15, 1996).

R. Sanchez-Gonzalez, R. Srinivasan, R.D.W. Bowersox, and S.W. North, "Simultaneous velocity and temperature measurements in gaseous flow fields using the VENOM technique," Opt. Lett. vol. 36, No. 2; 196-198 (Jan. 15, 2011).

J.A. Wehrmeyer, L.A. Ribarov, D.A. Oguss and R.W. Pitz, "Flame flow tagging velocimetry with 193-nm H2O photodissocation," Appl. Opt. vol. 38, No. 33; 6912-6917 (Nov. 20, 1999).

R. Miles, A. Dogariu, H. Rabitz, and J. Roslund, "Simultaneous Multiple Species Imaging by Femtosecond Multiphoton Laser Induced Fluorescence," SPIE Europe: Optics + Optoelectronics; (Apr. 20-23, 2009).

\* cited by examiner

FEMTOSECOND LASER EXCITATION TAGGING ANEMOMETRY

CROSS-REFERENCE TO PRIOR FILED APPLICATION

This application claims priority to an earlier filed provisional application 61/482,015 filed on May 3, 2011, which is herein incorporated by reference in its entirety.

UNITED STATES GOVERNMENT RIGHTS

This invention was made with government support under U.S. Air Force Office of Scientific Research contract FA9550-09-1-0236. The United States government has certain rights in this invention.

FIELD OF THE DISCLOSURE

The present disclosure generally relates to a new process for imaging high speed flow including turbulent structures.

BACKGROUND

The measurement of velocities in turbulent and reacting flows is essential for the fundamental understanding and optimization of modern combustors and vehicles. Typical measurement techniques for unsteady flows infer the velocity from pressure, heat transfer or particle movement. They consist of pitot tube pressure measurements, hot wire anemometry, particle imaging velocimetry and laser Doppler velocimetry. These techniques have been applied with great success to a wide array of flows, but have drawbacks since they do not directly measure the molecular motion. Pitot tube and hot wire approaches have limited spatial resolution due to the size of the probes. Particle scattering measurements are not continuous and there are strict requirements for particle seeding: particle size must be carefully controlled to assure that the particles follow the flow accurately and the seeding density must be controlled to provide adequate sampling while avoiding secondary scattering and aliasing.

As an alternative to the techniques mentioned, a number of velocity measurement techniques have recently been applied by directly tracking velocity from molecular motion. These techniques have targeted a number of different molecular species. The first approach for tracking molecules in unseeded air was the RELIEF technique which used two color Raman excitation and laser-induced electronic fluorescence to track molecular oxygen (R. Miles, C. Cohen, P. Howard, S. Huang, E. Markovitz, and G. Russell, "Velocity Measurements by vibrational tagging and fluorescent probing of oxygen," Opt. Lett. 12, 861-863 (1987); R. B. Miles, J. J. Connors, E. C. Markovitz, P. J. Howard and G. J. Roth, "Instantaneous profiles and turbulence statistics of supersonic free shear layers by Raman excitation plus laser-induced electronic fluorescence (RELIEF)," Exp. in Fluids 8, 17-24 (1989); R. B. Miles, J. Grinstead, R. H. Kohl, and G. Diskin, "The RELIEF flow tagging technique and its application in engine testing facilities and in helium-air mixing studies," Meas. Sci. Tech. 11, 1272-1281 (2000)). RELIEF takes advantage of the long lifetime of vibrationally excited oxygen. The air photolysis and recombination tracking (APART) technique (N. Dam, R. J. H. Klein-Douwel, N. M. Sijtsema, and J. J. ter Meulen, "Nitric oxide flow tagging in unseeded air," Opt. Lett. 26, 36-38 (2001)) uses a UV laser to dissociate oxygen and form nitric oxide, which is tracked by laser induced fluorescence. The vibrationally excited NO monitoring (VENOM) technique uses photodissociation of seeded $NO_2$ to produce vibrationally excited NO, which is subsequently imaged by LIF after a delay (R. Sanchez-Gonzalez, R. Srinivasan, R. D. W. Bowersox, and S. W. North, "Simultaneous velocity and temperature measurements in gaseous flow fields using the VENOM technique," Opt. Lett. 36, 196-198 (2011)). The vibrational excitation allows the tagged NO to be distinguished from background NO. VENOM also has the capability of measuring temperature from the NO fluorescence spectrum. Other molecules which have been tagged for velocimetry include ozone (R. W. Pitz, T. M. Brown, S. P. Nandula, P. A. Skaggs, P. A. DeBarber, M. S. Brown, and J. Segall, "Unseeded velocity measurement by ozone tagging velocimetry," Opt. Lett. 21, 755-757 (1996); R. W. Pitz, J. A. Wehrmeyer, L. A. Ribarov, D. A. Oguss, F. B. Batliwala, P. A. DeBarber, S. Deusch and P. E. Dimotakis, "Unseeded molecular flow tagging in cold and hot flows using ozone and hydroxyl tagging velocimetry," Meas. Sci. and Tech. 11, 1259-1271 (2000)), biacetyl (B. Hiller, R. A. Booman, C. Hassa, and R. K. Hanson, "Velocity visualization in gas flows using laser-induced phosphorescence of biacetyl," Rev. Sci. Inst. 55, 1964-1967 (1984)), and water vapor (L. R. Boedeker, "Velocity measurement by $H_2O$ photolysis and laser-induced fluorescence of OH," Opt. Lett. 14, 473-475 (1989); J. A. Wehrmeyer, L. A. Ribarov, D. A. Oguss and R. W. Pitz, "Flame flow tagging velocimetry with 193-nm H2O photodissocation," Appl. Opt. 38, 6912-6917 (1999)). Similar approaches have been demonstrated in water (W. R. Lempert, P. Ronney, K. Magee, R. Gee, and R. P. Haughland, "Flow tagging velocimetry in incompressible flow using photo-activated nonintrusive tracking of molecular motion (PHANTOMM)," Exp. in Fluids 18, 249-257 (1995); M. M. Koochesfahani, R. K. Cohn, C. P. Gendrich, and D. G. Nocera, "Molecular tagging diagnostics for the study of kinematics and mixing in liquid phase flows," in Proceedings of 8th International Symposium on Applications of Laser Techniques to Fluid Mechanics, Vol. 1 (1996) pp. 1.2.1-1.2.12 also in Developments in Laser Techniques and Fluid Mechanics, R. Adrian, et al., eds. (Springer-Verlag, 1997)). Applications of RELIEF enabled the measurement of turbulent fluctuations (A. Noullez, G. Wallace, W. Lempert, R. B. Miles and U. Frisch, "Transverse velocity increments in turbulent flow using the RELIEF technique," J. Fluid Mech. 339, 287-307 (1997)) and parameters of underexpanded supersonic jets (R. B. Miles, J. Connors, E. Markovitz, P. Howard and G. Roth, "Instantaneous supersonic velocity profiles in an underexpanded jet by oxygen flow tagging," Phys. Fluids A 1, 389-393 (1989)).

Previous work has used a ultraviolet nanosecond laser to photoionize molecular species and an ion probe to measure velocity (J. M. Ross, G. Laufer, and R. Krauss, "Laser Ion Time of Flight Velocity Measurements Using N2+Tracers" AIAA Journal, Vol 33, #2, February 1995, pp 296-300).

SUMMARY OF THE INVENTION

An apparatus for the imaging of gaseous fluid motion is disclosed. The apparatus includes a sub-nanosecond pulsed laser. The sub-nanosecond pulsed laser is configured to cause a particle species to fragment and for the recombining fragments subsequently to fluoresce. The apparatus also includes a gaseous fluid comprised of particle species. The apparatus also includes a time gated camera. The time gated camera configured to capture at least one image of the fluorescence from the recombining particle fragment species displaced after a specific time lapse following the laser pulse. Additionally, a fluid velocity can be calculated from a comparison of the image of the displaced particle species to an initial reference position and the time lapse.

The pulsed laser used in the apparatus may be a sub-picosecond laser, or a pulsed laser with a pulse length below 250 fs. The pulse from the pulsed laser may have an energy above 1 mJ. The time lapse following the laser pulse may be between about 0 µs to about 20 µs, or it may be between 0 µs to about 5 µs. The apparatus may also comprise a plurality of lasers.

The gaseous fluid of the apparatus may comprise nitrogen. Nitrogen may serve as the particle species in the apparatus. The gaseous fluid may be comprised of air. Also the gaseous fluid may comprise products of combustion in air.

The time gated camera of the apparatus may have a time gate of between 0 µs to about 5 µs, or the time gate may be about 1 µs. Also, the time gates camera may be configured to capture a plurality of time delayed images of the fluorescence, wherein a time sequenced series of images of the motion of the gaseous fluid is produced. The camera may also capture an image of the laser beam path during the laser pulse. The camera may also simultaneously image the fluorescence from different angles.

A Femtosecond Laser Electronic Excitation Tagging (FLEET) method is also disclosed. The FLEET method involves the step of identifying a gaseous fluid comprising particle species. The FLEET also involves the step of exposing the gaseous fluid to a sub-nanosecond laser pulse to fragment the particle species and for the recombining fragments subsequently to fluoresce. Another step of the FLEET method is capturing with a time gated camera at least one image of the fluoresced recombining fragment species separated in time by a known duration from the instant of exposure of the particle species to the laser pulse. Also the FLEET method has a step of determining the displacement of at least of one fluoresced fragment species from its location at the time of the instant of exposure of the particle species to the laser pulse and the instant of the image capture by the camera. The FLEET method may additionally include the step of using the displacement and the time lapse to determine at least one velocity component of the gaseous fluid.

The FLEET method may capture the image of the fluoresced particle species in the spectral range from approximately 560 to 660 nm. The FLEET method may also use two time-gated cameras to capture images of the fluoresced particle species. The FLEET method may use a laser with a pulse length below 1 picosecond or a laser with a pulse having energy above 1 mJ. The FLEET method may use a time gated camera that has a delay of between about 0 µs to about 20 µs after the laser pulse. Also it may use a time gated camera that has a delay of between about 0 µs to about 5 µs after the laser pulse. The time gated camera used in the FLEET method may have a time gate of about 1 µs. The FLEET method may include the step of capturing a plurality of time delayed images of the fluorescence. The FLEET method also may include the step of organizing the plurality of images into a time sequenced series of images of the motion of the gaseous fluid. The FLEET method may also include the steps of capturing an image at the instant of exposure of the particle species to the laser pulse ($T_0$ image) and using the $T_0$ image to measure the displacement of at least one particle species. The FLEET method may also include determining the velocity of the gaseous fluid is determined in two or three dimensions. The FLEET method may include an array of sub nanosecond lasers beams and the step of exposing the gaseous fluid to a laser pulse from an array of sub-nanosecond lasers to fluoresce the particle species. The FLEET method may include the step of simultaneously capturing images the fluorescing particle species from different angles.

The FLEET method may be used when the particle species comprises nitrogen. Also the FLEET method may be used when the gaseous fluid is air. Additionally, the FLEET method may be used when gaseous fluid comprises the products of combustion in air.

DETAILED DESCRIPTION OF THE INVENTION

Definitions

Figure 1:
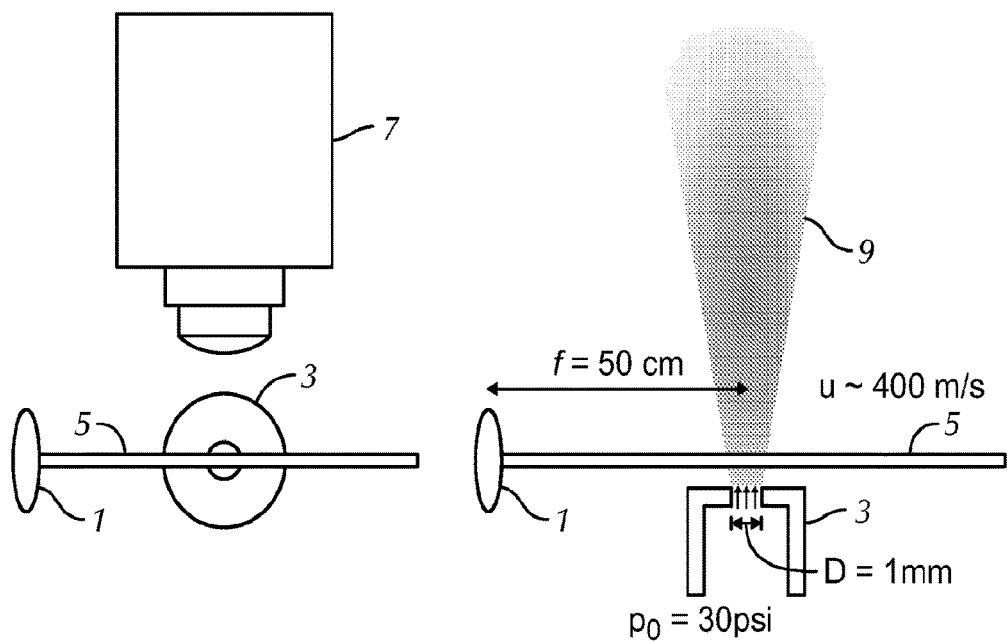
FIG. 1 is a schematic of a setup of the described apparatus showing a top view on the left and a side view on the right.

As used herein, the acronym "FLEET" refers to femtosecond laser electronic excitation tagging.

As used herein, the initials "PMT" refers to a photomultiplier tube.

As used herein, the initials "ICCD" refers to intensified charge-coupled device.

As used herein, the initials "psi" refers to the unit of pressure: pounds per square inch. This unit can be converted into atmospheres which are abbreviated herein "atm".

As used herein, the term "particle species" refers to an atom or molecule that is fluoresced by a sub-nanosecond laser as described in techniques and apparatus disclosed. Herein, the terms "Particle species" and "fluoresced species" are used interchangeably.

Disclosed is a process that uses nitrogen in naturally occurring air or other molecular species in a gaseous flow to create a line image whose displacement provides a precise measure of the flow velocity profile. The disclosed process uses a focused, sub nanosecond pulsed laser to dissociate molecules, producing atoms or other molecular fragments which subsequently recombine, producing fluorescence. The recombination and fluorescence processes last many microseconds, leading to fluorescence that persists for times long enough for the displacement for the flow to be recorded.

The energy of the laser is low, and it is not tightly focused, so a long line (centimeters in length) can be excited without producing any spark or significant change in the nature of the flow. The laser does not need to be tuned into resonance with any specific molecular transition.

For the quantification of the flow, the fluorescence is imaged by a time gated camera. The delay between the laser pulse and the gate time of the camera allows the flow to evolve before the image is taken.

The disclosed process enables the measurement of flow velocity and other gas properties through femtosecond molecular tagging. The sub nanosecond laser has high intensity through the focal zone, which provides a mechanism for the excitation and/or dissociation of all molecular species that are naturally occurring in the flow through multi-photon absorption, so no seeding is required and the laser does not need to be tuned in frequency. In addition, the laser has a pulse length short enough and energy low enough to avoid breakdown, so long lines can be written without perturbing the flow in any significant manner. The process is robust to high temperatures and will operate over a wide range of pressures.

The recombination of the molecular fragments takes many microseconds, so the displacement of the tagged line with time can be recorded with a camera. Time gating the camera provides the capability of following the precise location of the line as a function of the time following tagging. By accurately knowing the time between tagging and observation and measuring the line displacement distance, the velocity profile of the flow is determined. The vector component of the velocity profile measured is perpendicular to the line and in the plane normal to the camera axis. By focusing multiple laser beams into the flow or by refocusing a single beam, multiple lines, crosses and grid patterns can be written, and the measurement of their displacements provides a method for the measurement of other transport properties including vorticity, shear stress, dilatation, etc.

Referring to FIG. 1, the flow-tagging test setup consists of the laser (1) producing a laser beam focused across a vertically oriented free jet (3) operated with a 1 mm exit diameter, a 2.04 atm (30 psi (gauge)) plenum pressure, and uses compressed dry air. The laser causes a species of atoms or molecules within the gaseous fluid to dissociate. Subsequently, the recombining fragments fluoresce, producing a line of fluoresced species of atoms or molecules (5). A camera (7) is positioned to capture images (not shown) of the fluoresced species of atoms or molecules (5). A qualitative depiction of the free jet expansion (9) is shown. In the configuration depicted, the fluorescence (5) is observed over an approximately 1 cm length across the high-velocity jet (3). In the depicted example, the average velocity one diameter downstream of the exit is approximately 400 m/s. The jet (3) is placed on a vertical translation stage allowing the tagging of molecules at different stream-wise locations from the jet exit.

This approach measures the velocity or the velocity profile in a single laser pulse, and thus can capture details of the turbulent character of the flow.

To determine three dimensional movement, a second camera can be used. With the use of two or more cameras, a second component of the velocity profile can be simultaneously acquired. Additionally, the laser can be configured to produce a cross or pattern in the air for more precise or planar measurements of velocities.

For applications in air, the predominant fluorescing species is nitrogen which is formed in an upper electronic state when two nitrogen atoms combine. The fluorescence from this state is in the red to infrared portion of the spectrum and due to the time required for the atoms to recombine, it persists for ~25 microseconds in ambient pressure air. Lines have a width on the order of 50 microns. By fitting the transverse line profile, the line center can be determined to better than 10 microns, so even with a few microsecond delay, accurate measurements of the velocity profile can be made.

Figure 2:
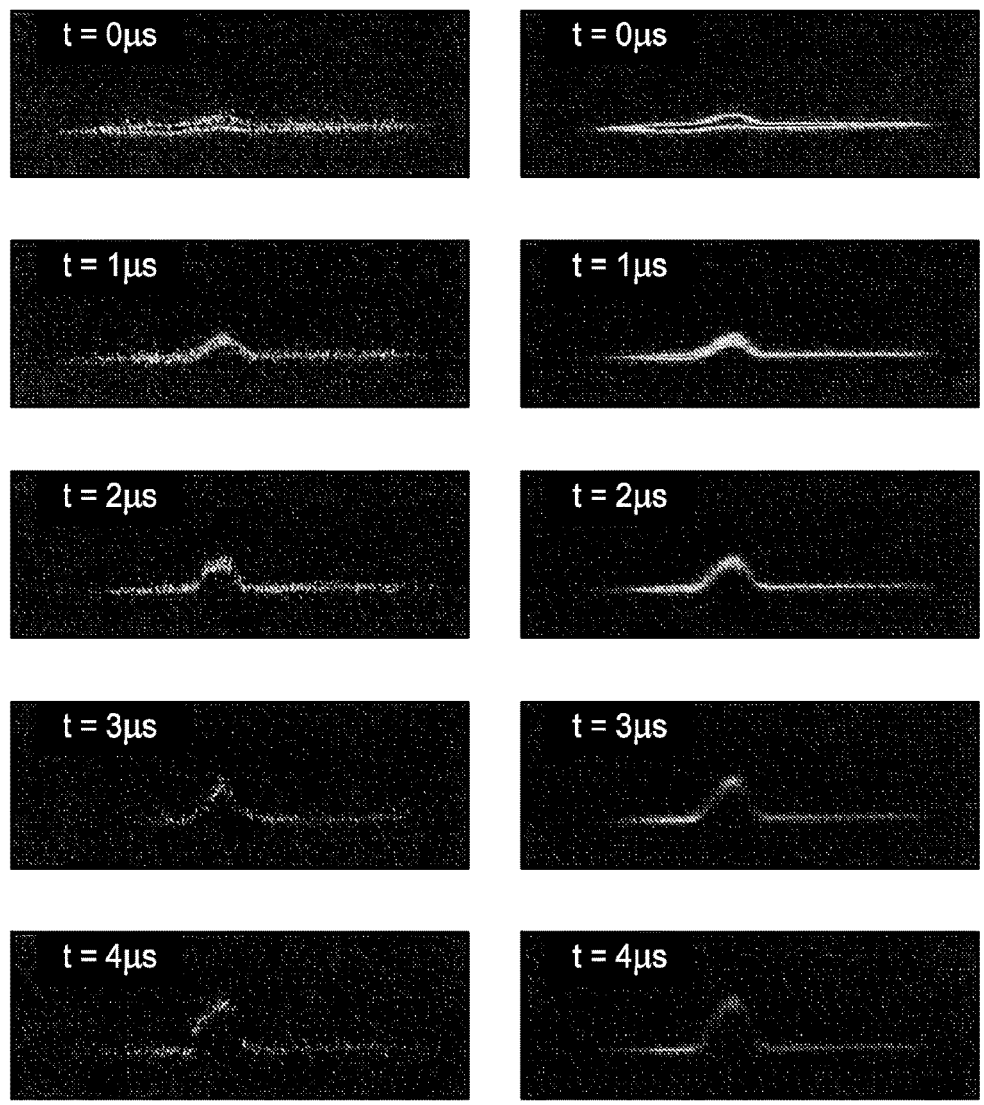
FIG. 2 is a series of time-lapse photos depicting the the measurement of the velocity of an air-jet. Displaced lines from femtosecond laser excitation tagging of nitrogen in air. The line is written across the exit of a small air jet. The images show instantaneous (left) and time averaged (right) motion of the line with the camera gate time delayed by 0, 1, 2, 3 and 4 microseconds. The laser is operated at 200 fs and focused with a 50 cm lens to form a ~1 cm long line; the 0 is offset from true 0 by a small time interval from the excitation laser to avoid saturation of the camera from laser Rayleigh scattering; by measuring the displacement, the centerline velocity of the jet is found to be 300+/−20 m/s.

FIG. 2 shows an example of the measurement of the velocity profile across the centerline of a small 300 m/sec air jet. A fast camera can capture sequential motions steps of a single tagged line, providing quantitative details on the transport of the flow.

One embodiment features an apparatus for the imaging of gaseous fluid motion comprising: a sub nanosecond pulsed laser beam which is focused into the gaseous fluid such that some of the molecular species along the laser path through the focal zone are caused to be fragmented by nonlinear absorption of laser light. A time gated camera is implemented that is capable of imaging luminosity from said gaseous medium as the atomic or molecular fragments combine and emit light, thus providing an image of the displacement of the gaseous fluid due to its motion during the time interval between the laser fragmentation and the camera imaging. In many applications the gaseous fluid contains nitrogen for which the fragments are nitrogen atoms, which recombine emitting light in the red and near infrared portion of the visible spectrum. In many applications the gaseous fluid containing nitrogen is simply air. In other applications, the gaseous fluid contains the products of combustion in air. This basic configuration can be augmented to obtain additional information or provide additional features.

For instance, the embodiment can further comprise a camera that captures multiple time delayed images of the emitted light, thus providing a time sequenced series of images of the motion of the gaseous fluid. From the image or images a velocity of fluoresced particles can be calculated. It can be extrapolated that the velocity of the fluoresced particles within the gaseous fluid is indicative of the movement of the gaseous fluid itself.

In some embodiments of the basic configuration the apparatus also comprises a camera that captures an immediate image of the original laser beam path and a time delayed image of the emitted light, thus providing an undisplaced reference and a displaced image of the gaseous fluid so accurate measurement of the displacement can be achieved. In this configuration, again the velocity of fluorescent particles can be calculated from the image or images.

Another embodiment is similar to the above but further features an array of sub-nanosecond laser beams such that a pattern of fragmented molecules is created and a time gated camera that images said pattern, providing further information on the motion of the gaseous fluid.

In yet another embodiment of the basic configuration features more than one camera that simultaneously image the displacement of the molecular fragments from different angles, thus providing the capability for three dimensional tracking of the motion of the gaseous fluid.

Another approach to acquire three dimensional tracking is to add to the basic configuration a single camera that simultaneously images the displacement of the molecular fragments from different angles, thus providing the capability for three dimensional tracking of the motion of the gaseous fluid.

Laser

Almost any extremely short duration laser that pulses with a duration under 1 nanosecond can be used with the described techniques and apparatus. It is understood and demonstrated that pulses with durations under 1 picosecond (ps) work well with the described techniques and apparatus. It is understood and demonstrated that pulses with durations under 250 femtosecond (fs) work well with the described techniques and apparatus. Some of the examples discussed herein use a laser configured to provide a pulse with a duration of about 120 fs.

For some of the examples discussed here, fluorescence was obtained using an amplified 120 fs pulse from a Spectra-Physics Mai Tai titanium-sapphire oscillator and a Coherent Hidra Ti:sapphire amplifier with pulsed chirp compression. The system outputs 120 fs, 1.2 mJ pulses centered at 810 nm at a 10 Hz repetition frequency. The laser is focused by a 50 cm plano—convex lens in air to a beam waist of 30 μm, resulting in a fluorescent region with a length of ~1 cm. The intensity in the focal volume is approximately $1 \times 10^{18}$ W per $m^2$. Unless specified, this is the laser that was used in the examples contained herein.

Sub-nanosecond lasers are well known in the art. These extremely short duration laser pulses are generally achieved through a technique referred to as mode-locking. The basis of the technique is to induce a fixed phase relationship between the modes of the laser's resonant cavity. The laser is then said to be "phase-locked" or "mode-locked". Interference between these modes causes the laser light to be produced as a train of pulses. Depending on the properties of the laser, these pulses may be of extremely brief duration, as short as a few femtoseconds.

Fluorescing Species and Fluorescence

A number of researchers have observed relatively long-lived emission from nitrogen in flowing systems—commonly referred to as the nitrogen Lewis—Rayleigh afterglow. Studies of nitrogen afterglow have been carried out in postglow discharges, postspark discharges, and postmicrowave discharges. These various generation methods have all shown evidence of significant populations of $N(^4S)$ atoms, which undergo three-body recombination to form unstable nitrogen $N_2(^5\Sigma^+_g)$ and subsequently, a vibrationally excited nitrogen B state ($v^0 \approx 11$) as described by Eqs. (1) and (2):

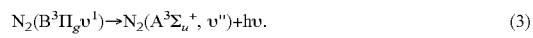

C. R. Stanley was the first to observe this afterglow at near-atmospheric pressure, where the first positive emission of nitrogen was observed in the range of 560 to 700 nm. These features correspond to the $\Delta v=3$ and $\Delta v=4$ bands of the first positive system of nitrogen for the transitions described by the equation 3. Emission from these bands has been observed at up to atmospheric pressure. The recombining nitrogen atoms repopulate the nitrogen B state, allowing the emission to continue for relatively long durations. Similar emission from recombining fragments of other molecular species may as well be used for other embodiments of this invention.

Figure 3:
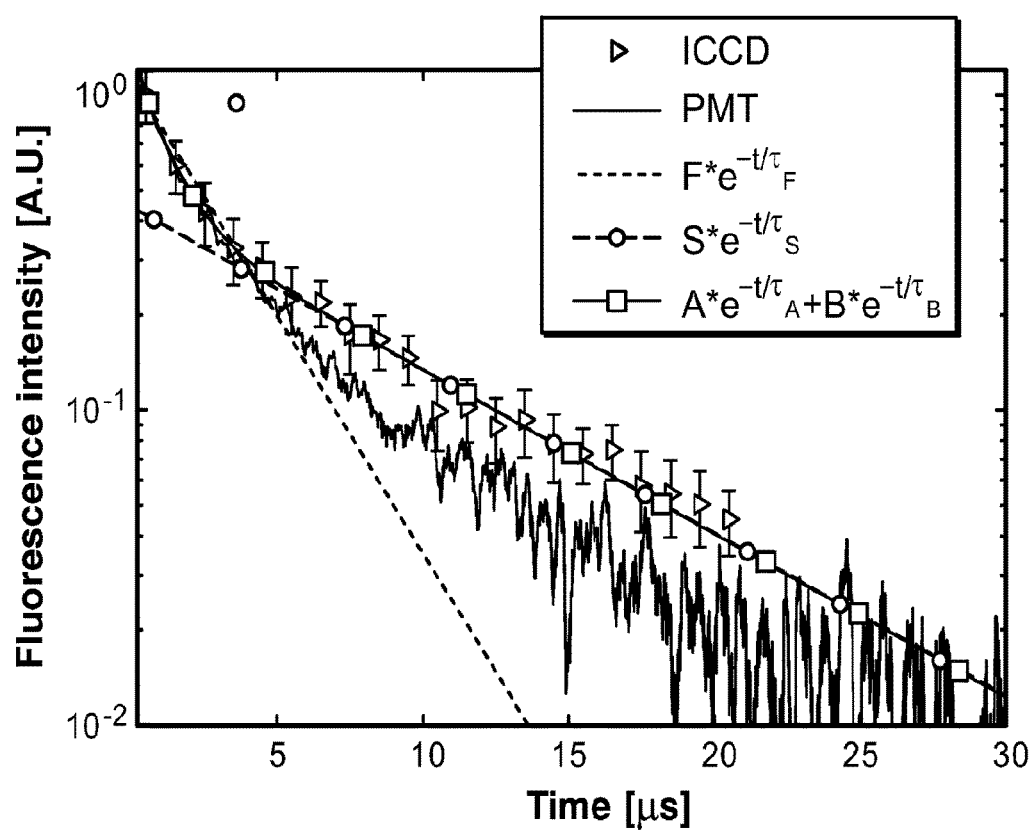
FIG. 3 is a graph of lifetime measurement of fluorescence with florescence intensity in units A.U. on the y-axis and time in µs on the x-axis.

In order to utilize molecular fluorescence for velocity determination, relatively long-lived emission from the recombination process is beneficial. Measurements indicate the initial decay of the first positive nitrogen fluorescence signal in air and determine a lifetime of approximately 4 μs by fitting an exponential. This signal arises from the initial formation of excited nitrogen molecules by the laser pulse. After that initial response, a long decay with a lifetime of tens of microseconds is observed. The long decay time associated with this emission is arises primarily from the time for atomic nitrogen to recombine into molecular nitrogen, a process that leads to molecular nitrogen in an electronically excited state. Examination of the fluorescence signal with a PMT and filter combination passing light from 560 to 660 nm resulted in good agreement with the signal recorded by sequentially time delayed images taken by the camera. As shown in FIG. 3, the fluorescence decay across the emission region exhibits a two-part behavior with rapid early decay and a subsequent slower decay. By fitting the ICCD signal with a dual exponential of the form A·exp($-t/t_A$)+B·exp($-t/t_B$) one can determine the decays of $t_A=1.1$ μs and $t_B=8.3$ μs or the two-part behavior. The PMT and ICCD decay rates show good agreement at long times with parallel behavior exhibited on the log scale. Bounding exponentials for the early and later decay are also shown in FIG. 3.

FIG. 3 depicts lifetime measurement of fluorescence in air with a bandpass-filtered PMT and the fast-gated ICCD with a 1 μs intensifier gate width. Emission allowing the determination of line position is evident at durations up to 30 μs after the femtosecond excitation laser pulse. The decays are bounded by a fast and slow exponential with lifetimes varying from $\tau_F$=0.8 μs for a fit at t≤5 μs and $\tau_S$=8 μs for long times. A dual exponential fit results in $t_A$=1.1 μs and $t_B$=8.3 μs.

The spectrum in the region of interest, from about 560 to 660 nm, exhibits features of the first positive system of nitrogen similar to those observed for flowing gas discharge systems at near-atmospheric pressures in nitrogen and air by previous investigators. (C. R. Stanley, "A new method for the production of active nitrogen and its application to the study of collision effects in the nitrogen molecular spectrum," Proc. Phys. Soc. A 67, 821-827 (1954).

J. F. Noxon, "Active nitrogen at high pressure," J. Chem. Phys. 36, 926-940 (1962).

K. D. Bayes and G. B. Kistiakowsky, "On the mechanism of the Lewis-Rayleigh nitrogen afterglow," J. Chem. Phys. 32, 992-1000 (1960).)

Camera

The collection of images of the displaced emission for FLEET does not require any specific camera, although it does require a fast-gated camera with fast and accurate timing and average or better sensitivity. The emission is not particularly bright and in general would only be quantifiable while using an intensified camera. For accurate measurements coordinated timing is also important. Sub microsecond accuracy on image capture delay and width is necessary for accurate measurements. To produce displacement images which are sharp and focused, a camera gate of about 1 μs or faster is preferable for typical flow velocities. If the described technique and apparatus are to be used for obtaining multiple images of the same line, a MHz rate camera is required since the emission last only microseconds.

An example of a suitable camera for use with the described technique and apparatus is the PI-MAX 512 ICCD (Princeton Instruments). The camera can be configured to capture a 512 by 512 pixel image. The camera can also be focused to give a resolution of 20-100 μm/pixel, which is a suitable resolution required to measure flow phenomena. The camera was modified to achieve the requisite timing. A laser timing system was added and configured Q-switch firing. The PI-Max is just one example of a suitable camera for use with the described techniques and apparatus. Other cameras have been successfully tested with the described system.

Calculating Velocity of a Fluid

The fact that the velocity is directly related to distance traveled in a known amount of time makes it possible to determine the instantaneous velocity. The calculation of the velocity uses the displacement and a time delay to the center of the 1 μs intensifier gate width as the time offset. The displacement of the fluorescence line at each position from the original straight line as determined by a Rayleigh scattering image results in an instantaneous velocity profile across the jet for each image. For quantitative determination of the velocity contour, at each radial location across the image a Gaussian profile can be fitted by a least-squares routine to determine the line center. The velocity can then determined by the difference between these Gaussian center fits and the Gaussian fit to the undisplaced Rayleigh scattering line image.

Figure 4:
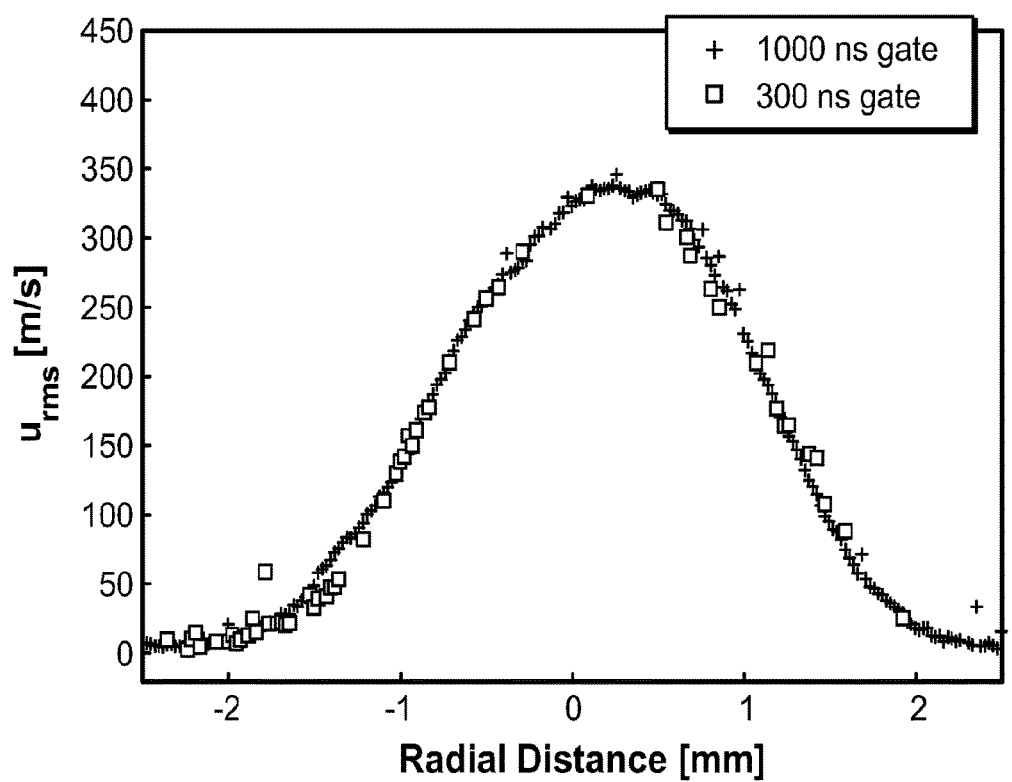
FIG. 4 is a graph comparing mean velocity profiles for y/D=10 for two intensifier gate widths of 300 and 1000 ns; the x-axis represents the magnitude of distance in mm units.

To verify that the intensifier gate width does not impact the determination of velocity, the gate width was varied between 300 ns and 1 μs and mean velocity profiles over 50 shots was determined. As shown in FIG. 4, the gate width did not impact the determined velocity. In one embodiment, a gate width of 1 μs was utilized in an effort to optimize signal strength and to minimize noise while retaining as much radial spatial resolution as possible. Over the 1 μs time interval, the change in fluorescence strength is negligible, indicating this time interval is suitable for use with the described techniques and apparatus.

Figure 5:
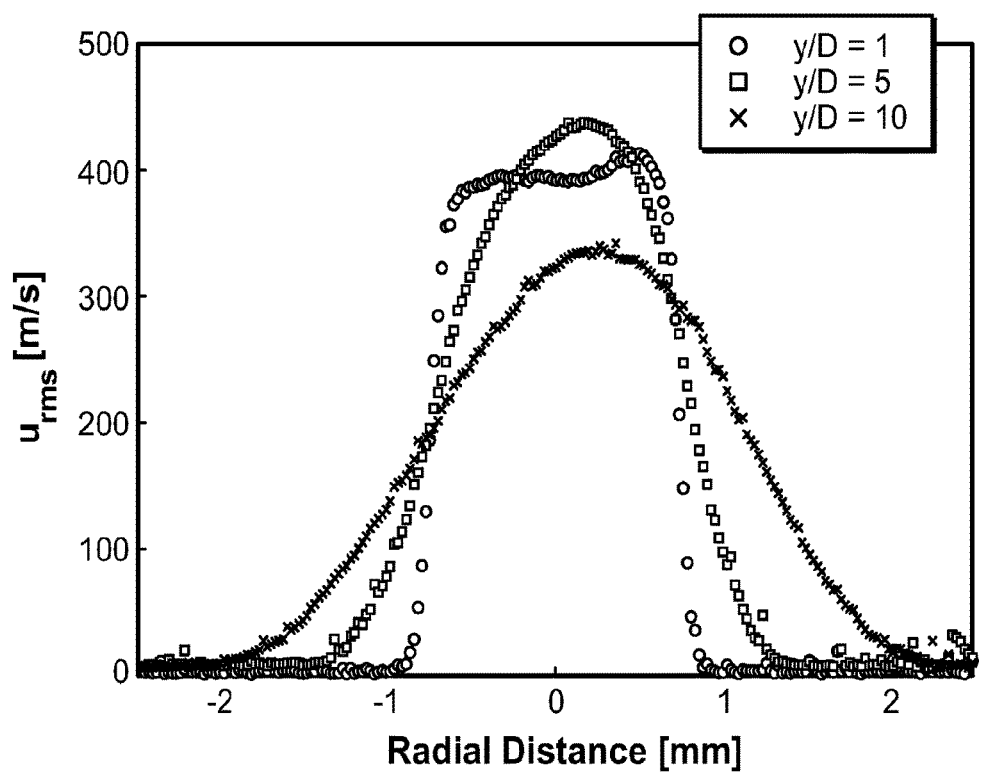
FIG. 5 is a graph depicting the mean velocities at y/D=1, 5, and 10 for a 1 µs gate, the camera gate delay is 2 µs and the velocity is determined by displacement from the Rayleigh scattering line; the x-axis represents the magnitude of radial distance in mm units.

Mean velocity profiles at different downstream locations above the nozzle exit are shown in FIG. 5. A plug profile is evident just above the jet exit (y/D=1) with jet expansion exhibited for farther downstream locations y/D=5 and 10. Mean velocities are averaged over 50 shots.

Figure 6:
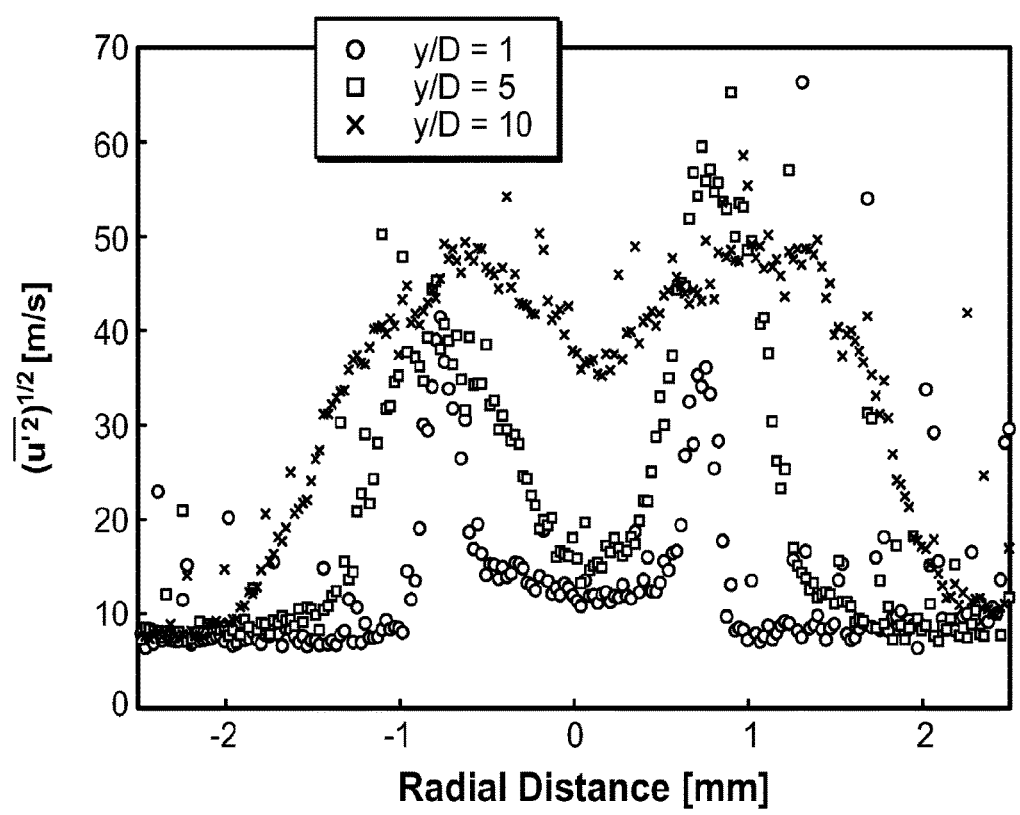
FIG. 6 is graph depicting the mean of velocity deviation from the mean at stream-wise locations at y/D=1, 5, and 10, the gate delay was set to 2 µs with a gate width of 1 µs; the x-axis marks the magnitude of radial distance in mm.
Figure 7:
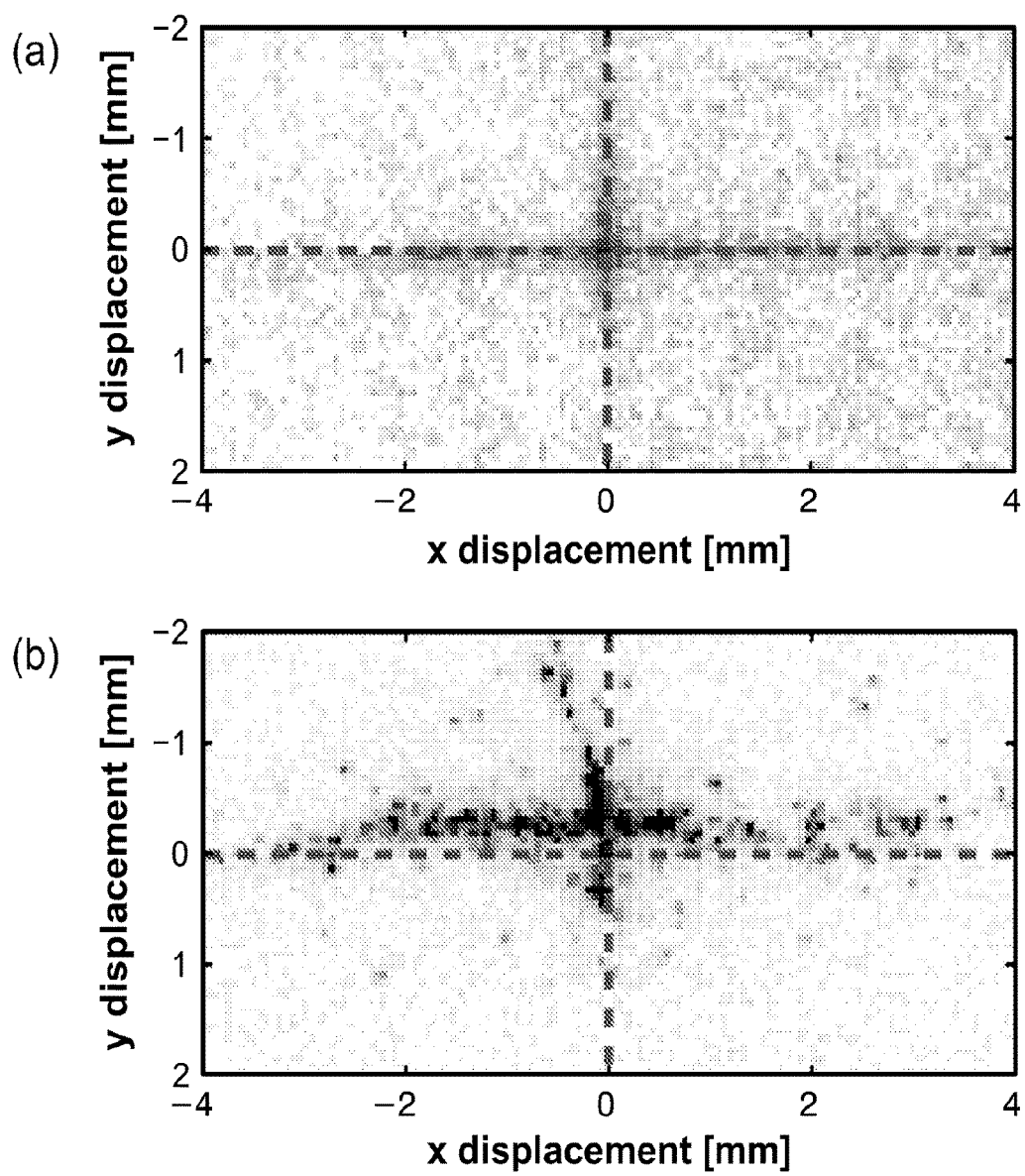
FIGS. 7a-b are images depicting an example of laser excitation grid for determination of multiple components of velocity in a single frame for a1 µs gate with a gate delay of 10 µs; in each image the x-axis and the y-axis each represent displacement in mm units.

These images can be used to determine the statistical properties of the flow. For example, FIG. 6 shows the time-averaged velocity fluctuations from the mean over 50 shots. The velocity fluctuation u' is defined as u'=u−U, where u is the instantaneous velocity and U is the mean velocity at a particular transverse location in the jet. The mean of the stream-wise velocity fluctuation is shown at axial locations y/D=1, 5, and 10. The velocity fluctuation profiles peak in the free shear layer with expansion of this free shear layer as we increase the distance from the jet exit. Operation of the jet with pure nitrogen leads to much brighter images, and operation with pure oxygen produces no observable long-lived fluorescence. Many lines, crosses, or grids can be written onto the air using multiple laser beams or multiple passages of a single laser pulse. Because of the very low attenuation of the laser, after the initial tagging the laser can be redirected back into the sample volume. An example of a cross for two-dimensional velocity determination is shown in FIG. 7. For this example, the laser was simply reflected back into the sample volume using mirrors: once vertically and once horizontally. The two images show (a) the Rayleigh scattering of the dual laser focusing and (b) the displacement of both of these fluorescent lines with a low mean velocity (10 m=s) air flow directed from the bottom right to upper left. The camera gate was set to 1 μs with a delay of 10 μs. The mean direction is evident from the displacement of the crossing point. The position of the focusing of the two laser beams is indicated by the thick dashed lines in both FIGS. 7(a) and 7(b). With a second camera, the three-dimensional velocity vector can be captured by following the motion of the crossing point in three dimensions. The rotation of the cross gives the local vorticity. With more complex structures, such as rectangles and grids, shear stress and dilatation can be measured and a full field transport measurement can be made.

EXAMPLES

The Examples presented herein are meant for an illustrative purpose and should not read as limiting of the claims that follow.

Example 1.

Small Underexpanded Jet.

Figure 8:
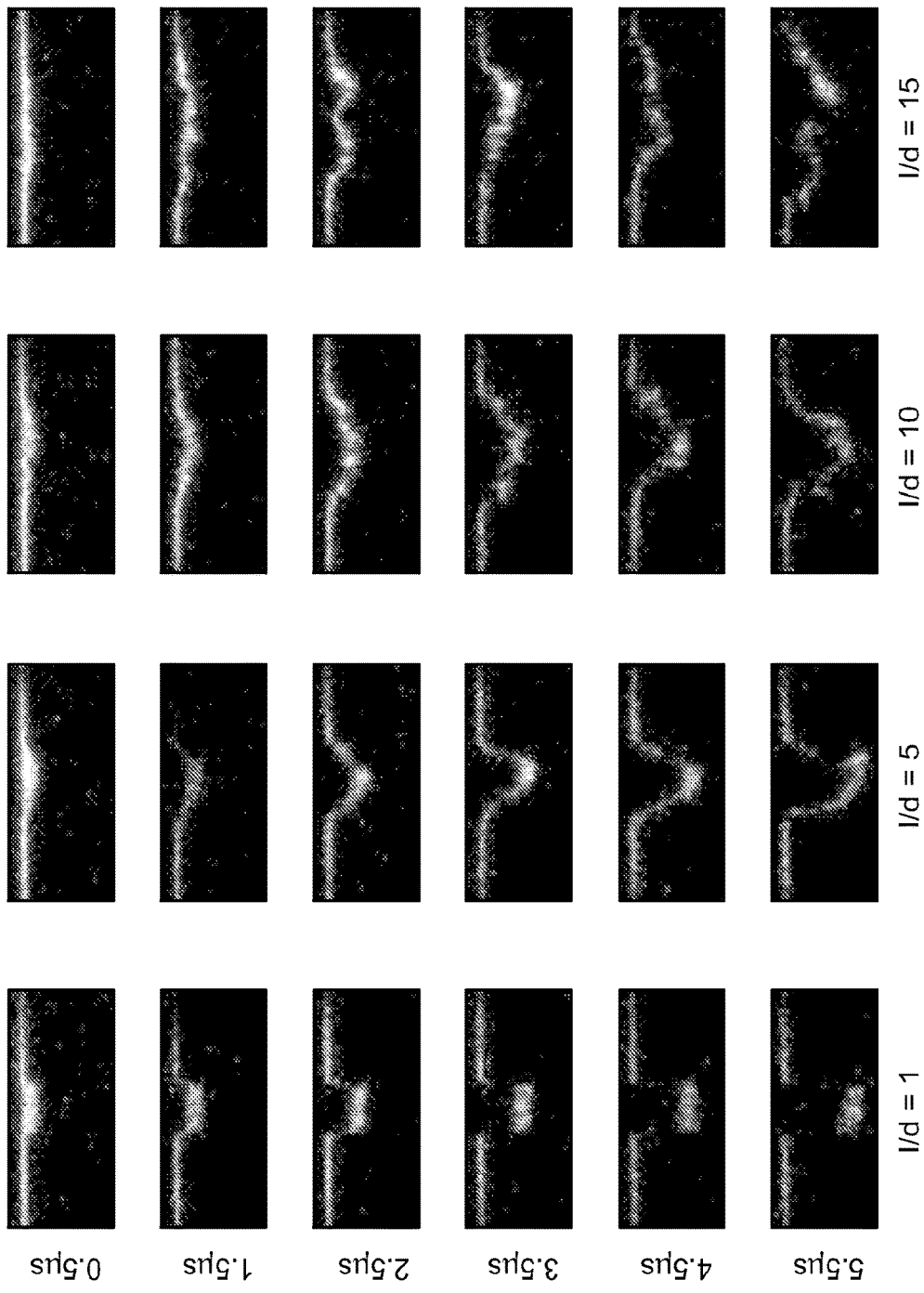
FIG. 8 is single shot images of displacement in flow taken with 1000 ns gate at delays between 0 and 5 µs; the time the image was taken is shown at left (gate delay added to half of gate width) and the distance along the flow of the laser to orifice diameter ratio are shown along the bottom of the chart.

FLEET was first demonstrated on a vertical 1 mm diameter free jet. The velocity at the jet exit was approximately 400 m/s, and the jet was mounted on a movable stage so that different regions of the flow could be imaged. The femtosecond laser was focused through a 50 cm plano-convex lens to a beam waste of 30 μm. Images were taken at camera delays between 0 and 5 μs and gate widths of 300 and 1000 ns. In FIG. 8 1000 ns images of the displaced line are presented at four different downstream positions and several different delays. In these images the flow velocity is directed downward. In the images captured further downstream, the changing structure of the nozzle flow is readily visible, demonstrating FLEET's ability to characterize flows.

Figure 9:
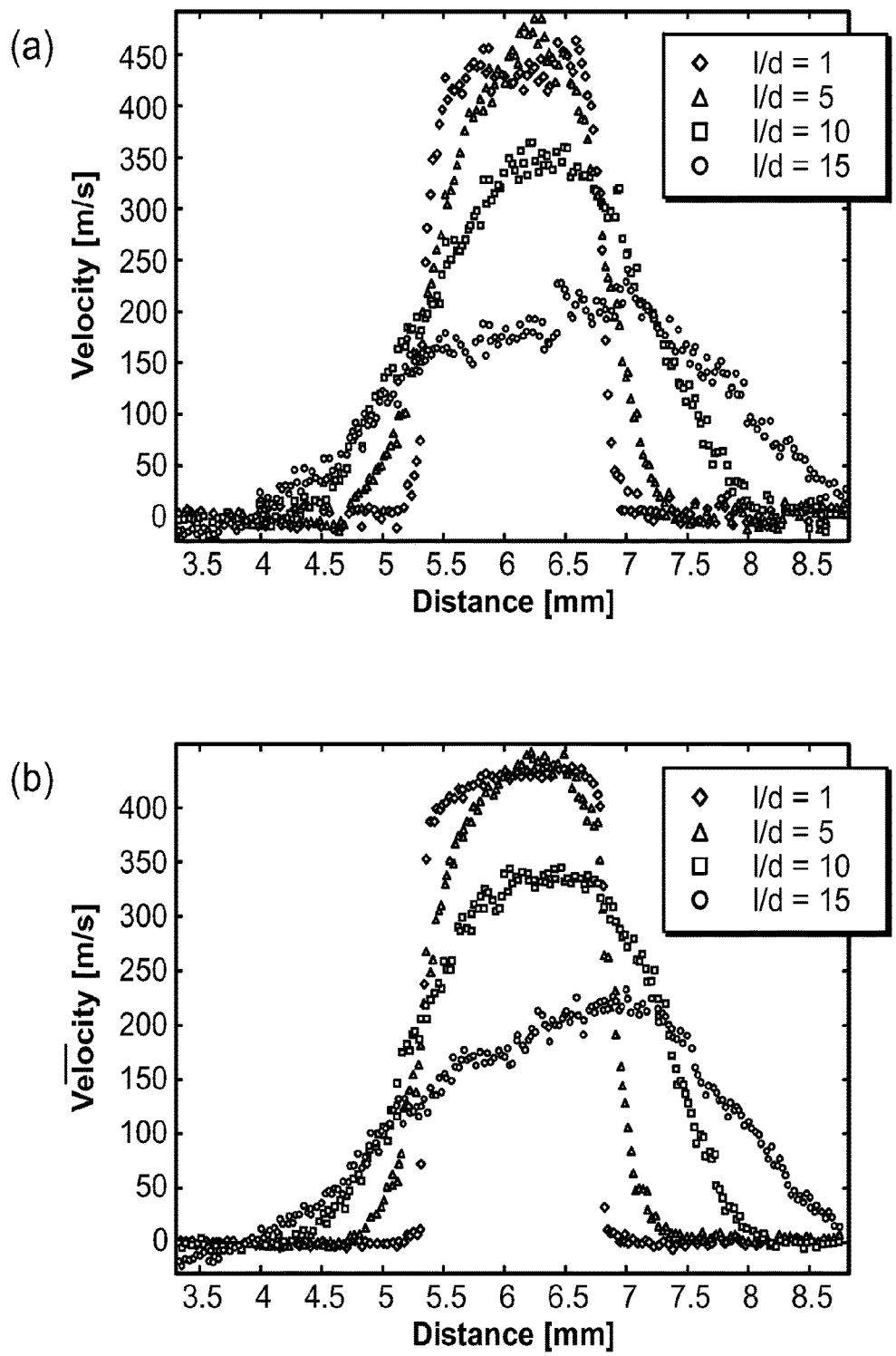
FIGS. 9a-b are graphs depicting average (median) velocity profiles for underexpanded jet calculated from 50 images; gate width was 1000 ns in (a) the gate delay is 1 µs and in (b) the gate delay is 5 µs; for both (a) and (b) the y-axis represents velocity in units of m/s, the x-axis represents distance in mm.
Figure 10:
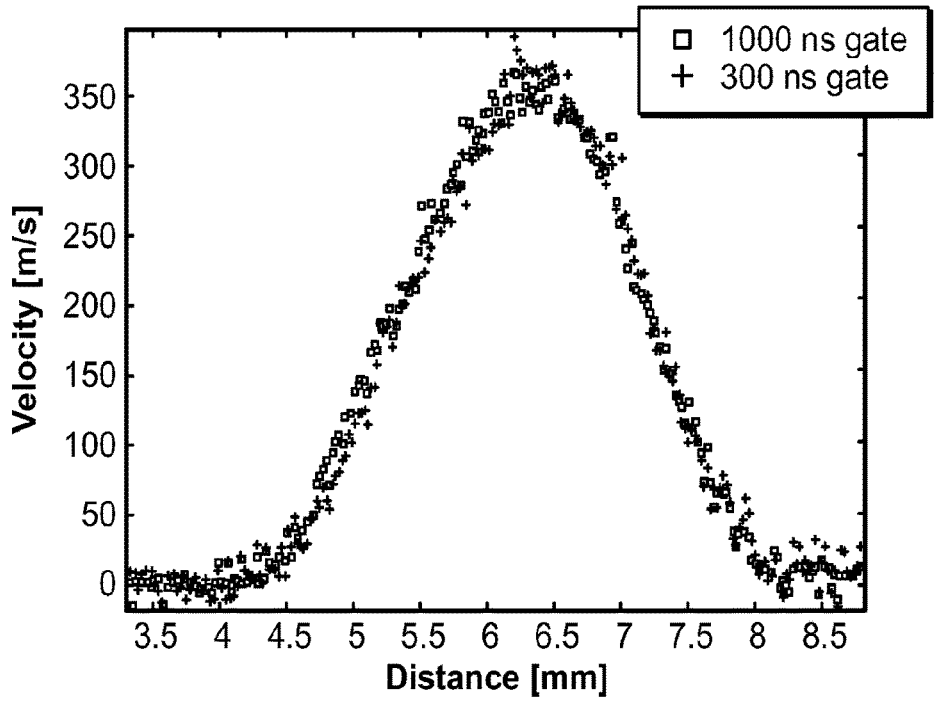
FIG. 10 is a graph depicting a comparison of velocities measured with 300 ns and 1000 ns gate width, gate delay is 1 µs, l/d is 10 and values are median value taken from sets of 50 images; the y-axis represents velocity in units of m/s, the x-axis represents distance in mm.
Figure 11:
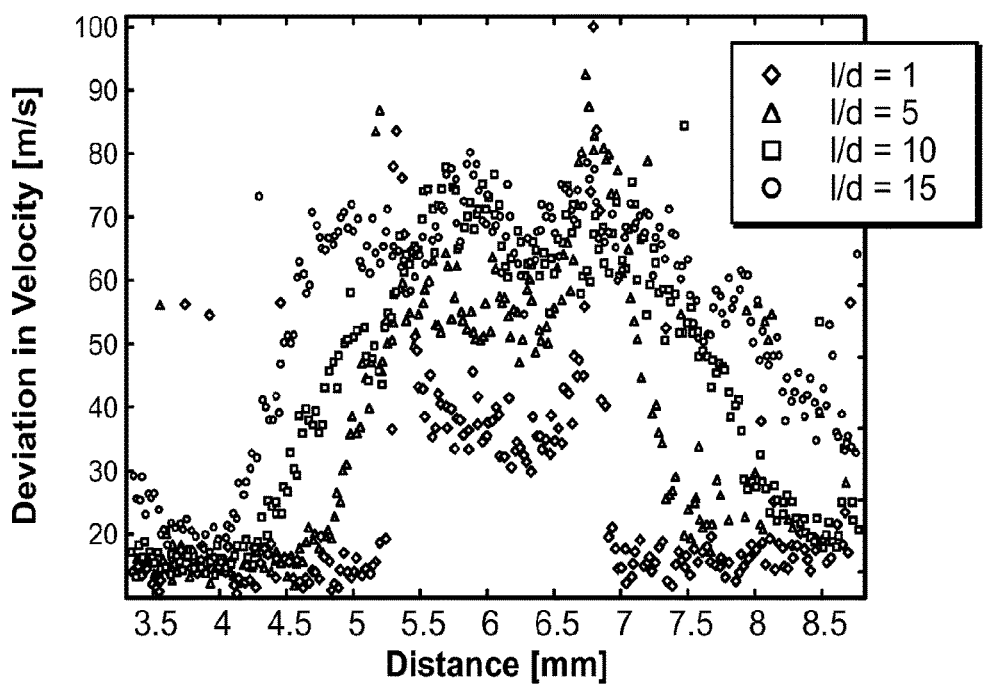
FIG. 11 is graph depicting the standard deviation of velocity measurements in air jet, the gate width was 1000 ns; the y-axis represents velocity in units of m/s, the x-axis represents distance in mm.

Images captured using FLEET provide the ability to extract velocities from the data. Such velocities have been calculated from the images shown in FIG. 8. FIG. 9 presents median velocities at each flow position downstream of the jet. The similarity between the velocities measured using gate delays of 1 and 5 µs demonstrate that there are no unexpected effects due to the camera delay. FIG. 10 demonstrates that artifact effects associated with gate width. Variations in camera gate and delay only generate noise, rather than affect mean velocity values. These velocities were individually calculated from single shot data and then averaged. In FIG. 11, the standard deviation of the calculated velocity values is plotted against transverse position. Here there is some level of variation due to noise in the fitting regime, it is clear that in this experiment the dominant source of variation in velocity values is due it real variations in the flow velocity; the areas of increased variation correspond to fluctuating regions of the flow.

Example 2.

Large Sonic Jet.

Figure 12:
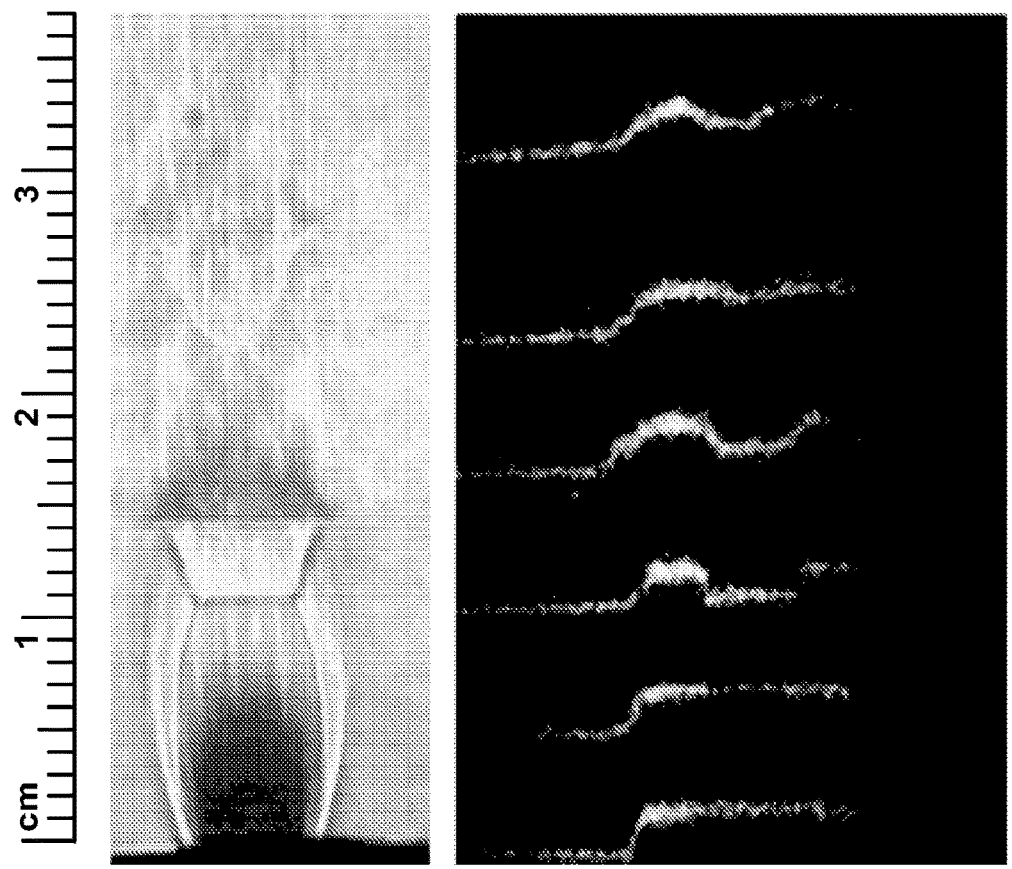
FIG. 12 is two images depicting Visualization and FLEET measurements of free jet flow at left is a shadow-graph of the flow out of a 6 mm nozzle at right is a composite of FLEET displacement images taken at different locations in the flow.

Velocity measurements were taken in a 6 mm vertically oriented under expanded free jet, whose flow is depicted in FIG. 12. These images were taken in an air flow at a plenum pressure of approximately 6.08 atm (100 psi), giving a nozzle exit velocity of approximately 300 m/s. The displaced FLEET lines shown at the right of the figure were captured at a 2 µs delay and 500 ns gate. The composite image is made from stills from a movie taken of the laser location being varied along the flow.

Figure 13:
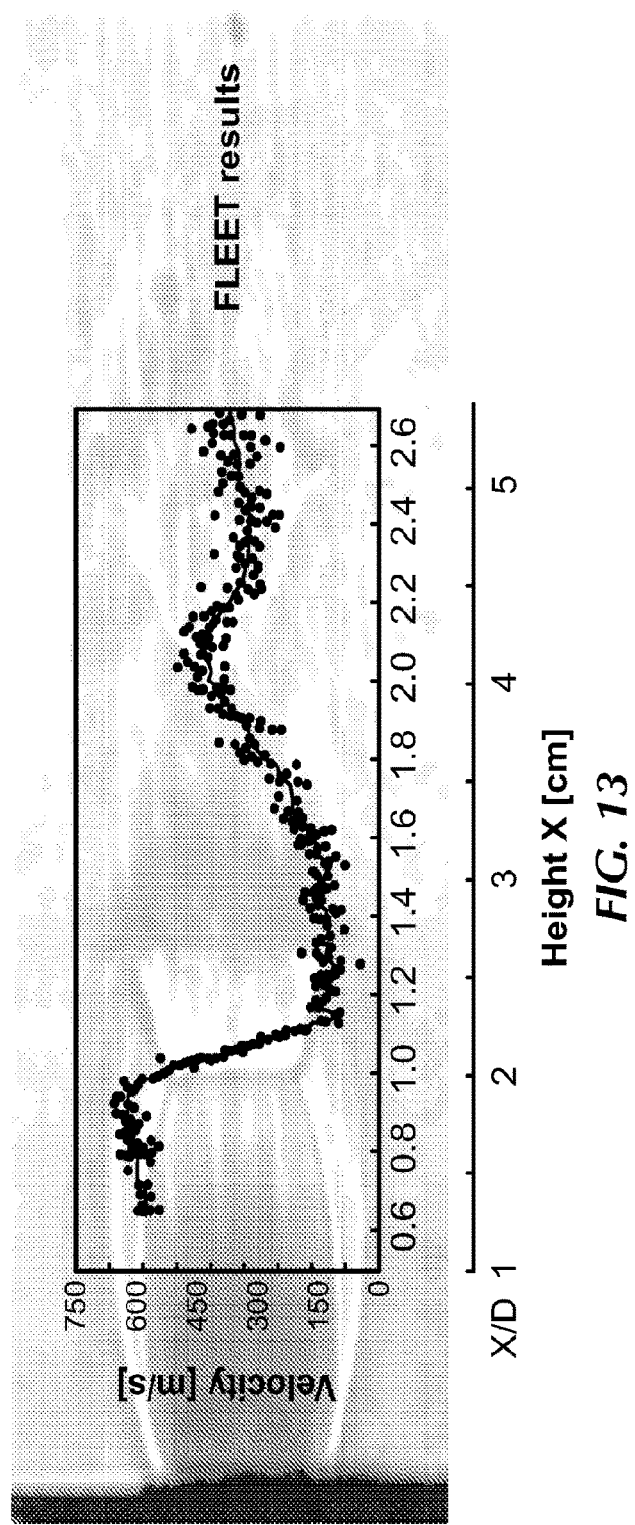
FIG. 13 is an image and overlay depicting centerline velocity measurements in free jet, these velocities were found by varying the location of the beam in a moving flow while continuously capturing images at a fixed time delay.

The centerline velocity profile measured using FLEET is plotted in FIG. 13. For this experiment, since there was no fixed initial line location, the initial position was found using extrapolation from a line fit to an unmoving segment of the tagged line. The left segment of the tagged lines in FIG. 12 are outside of the free jet, and are thus almost unmoving.

What is claimed is:

1. An apparatus for imaging of gaseous fluid motion comprising:
    a gaseous fluid comprising particle species;
    a sub-nanosecond pulsed laser configured to cause, in a single laser pulse, the particle species to fragment and recombining fragments subsequently to fluoresce; and
    a time gated camera wherein the time gated camera is configured to capture at least one image of the fluorescence from the recombining fragments displaced after a specific time lapse following the single laser pulse.

2. The apparatus of claim 1, wherein a fluid velocity is calculated from a comparison of the image of the displaced fragments to an initial reference position and the time lapse.

3. The apparatus of claim 1, wherein the laser is a sub-picosecond laser.

4. The apparatus of claim 1, wherein the laser has a pulse length below 250 fs.

5. The apparatus of claim 1, wherein the pulse from the pulsed laser has an energy above 1 mJ.

6. The apparatus of claim 1, wherein the time lapse is between about 0 µs to about 20 µs.

7. The apparatus of claim 1, wherein the time gated camera has a time gate of between 0 µs to about 5 µs.

8. The apparatus of claim 1, wherein the camera is configured to capture a plurality of time delayed images of the fluorescence, wherein a time sequenced series of images of the gaseous fluid motion is produced.

9. The apparatus of claim 1, wherein the camera also captures an image of a laser beam path during the laser pulse.

10. The apparatus of claim 1, further comprising a plurality of laser beams.

11. The apparatus of claim 1, wherein the camera simultaneously images the fluorescence from different angles.

12. The apparatus of claim 1, wherein the particle species comprises nitrogen.

13. The apparatus of claim 12, wherein the gaseous fluid comprises air.

14. The apparatus of claim 12, wherein the gaseous fluid comprises products of combustion in air.

15. A Femtosecond Laser Electronic Excitation Tagging (FLEET) method comprising:
    identifying a gaseous fluid comprising particle species;
    exposing the gaseous fluid to a single sub-nanosecond laser pulse to fragment the particle species and recombining fragments subsequently to fluoresce;
    capturing with a time gated camera at least one image of the fluoresced recombining fragments separated in time by a specific time lapse from an instant of exposure of the particle species to the single laser pulse;
    determining a displacement of at least one fluoresced fragment from its location at the time of the instant of exposure of the particle species to the single laser pulse and the instant of the image capture by the camera; and
    using the displacement and the specific time lapse to determine at least one velocity component of the gaseous fluid.

16. The FLEET method of claim 15, wherein the image of the fluoresced particle species is captured in a spectral range from approximately 560 to 660 nm.

17. The FLEET method of claim 15, wherein two time-gated cameras are used to capture images of the fluoresced particle species.

18. The FLEET method of claim 17, wherein the velocity of the gaseous fluid is determined in two or three dimensions.

19. The FLEET method of claim 15, wherein the laser has a pulse length below 1 picosecond.

20. The FLEET method of claim 15, wherein the pulse from the pulsed laser has an energy above 1 mJ.

21. The FLEET method of claim 15, wherein the time gated camera has a delay of between about 0 µs to about 20 µs after the laser pulse.

22. The FLEET method of claim 15, wherein the time gated camera has a time gate of between 0 µs to about 5 µs.

23. The FLEET method of claim 15 further comprising the following step: capturing a plurality of time delayed images of the fluorescence.

24. The FLEET method of claim 23 further comprising the following step: organizing the plurality of images into a time sequenced series of images of a gaseous fluid motion.

25. The FLEET method of claim 15 further comprising the following steps:
    capturing an image at the instant of exposure of the particle species to the laser pulse ($T_0$ image); and
    using the $T_0$ image to measure the displacement of at least one fluoresced fragment.

26. The FLEET method of claim 15 further comprising the following step: exposing the gaseous fluid to a laser pulse from an array of sub-nanosecond lasers to fluoresce the particle species.

27. The FLEET method of claim 15, comprising the following step: simultaneously capturing images of the fluorescing particle species from different angles.

28. The FLEET method of claim 15, wherein the particle species comprises nitrogen.

29. The FLEET method of claim 28, wherein the gaseous fluid comprises air.

30. The FLEET method of claim 28, wherein the gaseous fluid comprises products of combustion in air.

31. The apparatus of claim 1, wherein a line is written into the fluid by the laser and a fluid velocity profile is calculated from a comparison of the image of the line to an initial reference position and the time lapse.

32. The apparatus of claim 1, wherein a pattern is written into the fluid by the laser and fluid transport properties including at least one of velocity, vorticity, shear stress and dilatation are calculated from a comparison of the image of the pattern to an initial reference pattern and the time lapse.

33. The apparatus of claim 1, wherein the laser apparatus is pulsed multiple times and multiple images are recorded to determine fluctuating properties of the gaseous fluid motion.

34. The FLEET method of claim 15, further comprising: writing a line into the fluid by the laser and calculating a fluid velocity profile from a comparison of the image of the line to an initial reference position and the time lapse.

35. The FLEET method of claim 15, further comprising: writing a pattern into the fluid by the laser and calculating fluid transport properties including at least one of velocity, vorticity, shear stress and dilatation from a comparison of the image of the pattern to an initial reference pattern and the time lapse.

36. The FLEET method of claim 15, wherein fluctuating properties of fluid motion are determined by:
  causing the particles species to fragment and the recombining fragments subsequently to fluoresce multiple times; and
  capturing multiple images of the fluoresced recombining fragments.

* * * * *